United States Patent [19]

Sheppard et al.

[11] 4,042,773

[45] Aug. 16, 1977

[54] PEROXIDE FREE RADICAL INITIATORS CONTAINING ULTRAVIOLET LIGHT STABILIZING GROUPS

[75] Inventors: Chester S. Sheppard; Ronald E. MacLeay, both of Buffalo, N.Y.

[73] Assignee: Pennwalt Corporation, Philadelphia, Pa.

[21] Appl. No.: 680,546

[22] Filed: Apr. 27, 1976

Related U.S. Application Data

[60] Division of Ser. No. 435,622, Jan. 22, 1974, abandoned, which is a continuation of Ser. No. 98,893, Dec. 16, 1970, abandoned.

[51] Int. Cl.² .............................. C08F 4/36; C08F 4/34; C08F 12/08
[52] U.S. Cl. ............................... 526/208; 260/45.85 R; 526/199; 526/204; 526/213; 526/215; 526/216

[58] Field of Search ............... 526/183, 193, 196, 208, 526/210, 211, 225, 227, 232

[56] References Cited

U.S. PATENT DOCUMENTS

| 3,644,406 | 2/1972 | Sheppard | 260/192 |
| 3,706,818 | 12/1972 | Mageli | 260/885 |
| 3,931,143 | 1/1976 | MacLeay | 260/192 |

FOREIGN PATENT DOCUMENTS

| 878,841 | 10/1961 | United Kingdom | 526/219 |

Primary Examiner—Christopher A. Henderson

[57] ABSTRACT

Compounds which contain azo or peroxide linkages as well as the radical of an ultraviolet light stabilizing group are described. These compounds function as polymerization initiators which cause an ultraviolet light stabilization group to be chemically bound to the polymer.

7 Claims, No Drawings

PEROXIDE FREE RADICAL INITIATORS CONTAINING ULTRAVIOLET LIGHT STABILIZING GROUPS

This is division of application Ser. No. 435,622, filed 1/22/74 and now abandoned which in turn is a continuation of application Ser. No. 98,893, filed Dec. 16, 1970 and now abandoned.

THE DISCLOSURE

This invention relates to novel compounds which are free radical initiators as well as being ultraviolet light stabilizers.

It is well known that many ethylenically unsaturated monomers are polymerized by the use of free radical initiators, i.e., those having aliphatic azo or peroxide groups. It is also well known that many of the polymers resulting from the polymerization of such monomers are subject to degradation by ultraviolet light, and therefore require the presence of an ultraviolet light stabilizer to extend the useful life of such polymers. Normally, such stabilizers are added to the polymer by methods such as milling or other methods of physical mixing. In more recent times techniques of copolymerization have been employed by means of which unsaturated derivatives of certain ultraviolet light stabilizing compounds have been copolymerized with vinyl monomers to form a light stabilized polymer. The method of physically mixing the stabilizer and the polymer has always been unsatisfactory because the resulting two-phase system is incompatible. The stabilizing compound inevitably migrates to the surface of the polymer and becomes separated from the polymer by evaporation, leaching, or erosion.

The copolymerization technique is much more satisfactory than physically blending because it provides a chemically bound stabilizer which is not removed by physical processes. This method, however, has many inherent disadvantages due to the chemical equilibria involved in copolymerization reactions. The comonomer providing the stabilizer component must have its reactivity balanced against that of the principal comonomer and the concentrations of these two comonomers adjusted accordingly in order to produce a product having the desired amount of stabilizer. The copolymerization technique also normally produces a product having much more stabilizer incorporated into the polymer than is necessary, and this increases the cost of the final product markedly. Furthermore, many of the stabilizer comonomers have a tendency to homopolymerize rather than to copolymerize and thereby to result in a product lacking in homogeneity.

It is an object of the present invention to provide novel compounds which function both as a free radical initiator and as an ultraviolet light stabilizer. It is another object of this invention to provide a light stabilized polymer wherein the stabilizer is chemically bound to the polymer and is present in an economical and regulated amount. Still other objects will be apparent from the more detailed description of this invention which follows.

In accordance with this invention, there is provided a free radical initiator containing ultraviolet light stabilizing groups and having the formula:

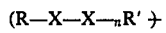

wherein —X—X— is —O—O— or —N═N—, R and R' are the same or different radicals, at least one of which comprises an ultraviolet light stabilizing radical, and n is 1 to 4.

PEROXIDES

In accordance with one preferred embodiment of this invention -X-X- is the peroxide group -O-O-. When $n=1$ in this embodiment R and R' are both selected from the group consisting of hydrogen, acyl of 2-20 carbon atoms, aroyl of 7-20 carbon atoms, t-alkyl of 4-12 carbon atoms, t-cycloalkyl of 4-12 carbon atoms, t-aralkyl of 9-15 carbon atoms, alkoxycarbonyl of 2-20 carbon atoms, cycloalkoxycarbonyl of 4-20 carbon atoms, carbamoyl, phenylcarbamoyl, alkylcarbamoyl of 2-13 carbon atoms, cycloalkylcarbamoyl of 4-13 carbon atoms, α-hydroxyalkyl of 2-10 carbon atoms, α-hydroxycycloalkyl of 3-10 carbon atoms, α-hydroperoxyalkyl of 2-10 carbon atoms, α-hydroperoxycycloalkyl of 3-10 carbon atoms, alkylsulfonyl of 4-20 carbon atoms, cycloalkylsulfonyl of 3-12 carbon atoms, t-(alkoxyalkyl) of 4-20 carbon atoms, t-(alkoxycycloalkyl) of 4-20 carbon atoms, and monovalent organomineral.

When $n=2$ in this embodiment R may be any of the radicals listed above for the condition of $n=1$, and R' is selected from the group consisting of carbonyl, alkylidene of 2-20 carbon atoms, cycloalkylidene of 3-12 carbon atoms, di-t-alkylene of 6-20 carbon atoms, di-t-cycloalkylene of 6-20 carbon atoms, di-t-aralkylene of 12-20 carbon atoms, and divalent organomineral.

When $n=3$ in this embodiment R may be any of the radicals listed above for the condition of $n=1$, and R' is selected from the group consisting of t-aralkyl-di-t-aralkylene of 15-20 carbon atoms, t-alkylalkylidene of 4-20 carbon atoms, t-cycloalkylalkylidene of 4-20 carbon atoms, t-alkylcycloalkylidene of 4-20 carbon atoms, t-cycloalkylcycloalkylidene of 6-20 carbon atoms, t-alkyl-di-t-alkylene of 10-19 carbon atoms, t-alkyl-di-t-cycloalkylene of 10-19 carbon atoms, t-cycloalkyl-di-t-alkylene of 10-19 carbon atoms, t-cycloalkyl-di-t-cycloalkylene of 10-19 carbon atoms, and trivalent organomineral.

When $n=4$ in this embodiment R may be any of the radicals listed above for the condition of $n=1$ and R' is dialkylidene of 5-16 carbon atoms. The mineral component in any of the organominerals mentioned above is selected from the group consisting of silicon, arsenic, antimony, phosphorus, germanium, boron, and tin.

AZO COMPOUNDS

In accordance with another preferred embodiment of this invention -X-X- is the azo group -N═N-. When $n=1$ in this embodiment R and R' are both selected from the group consisting of alkyl of 1-20 carbon atoms; cycloalkyl of 3-10 carbon atoms; aralkyl of 7-20 carbon atoms; and

wherein Y is selected from the group consisting of NC-,

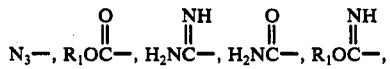

-continued

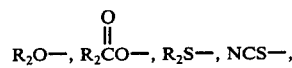

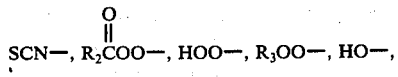

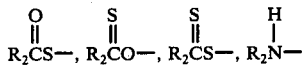

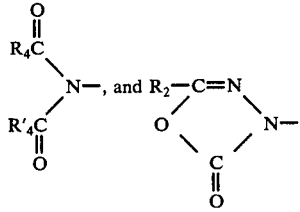

wherein R₁ and R₂ are selected from the group consisting of alkyl of 1-20 carbon atoms; cycloalkyl of 3-6 carbon atoms; alkylene of 2-30 carbon atoms when R₁ and R₂ are joined together; any of said alkyl, cycloalkyl, or alkylene containing as a substituent a member of the group consisting of carboxy, carboxy ester of 1-6 carbon atoms, hydroxy, and alkoxy of 1-6 carbon atoms; and wherein one but not both of R₁ and R₂ may in addition be phenyl, tolyl, xylyl, benzyl, or phenethyl; R₃ is t-alkyl of 4-8 carbon atoms, t-cycloalkyl of 4-8 carbon atoms, or t-aralkyl of 9-15 carbon atoms; R₄ and R₄' are alkyl of 1-6 carbon atoms, cycloalkyl of 3-6 carbon atoms, aryl of 6-12 carbon atoms when R₄ and R₄' are not joined together, and alkylene of 1-6 carbon atoms or arylene of 6-12 carbon atoms when R₄ and R₄' are joined together. Furthermore, with one exception, R, but not R', may also be selected from the group consisting of aryl of 6-14 carbon atoms, acyl of 2-20 carbon atoms, aroyl of 7-20 carbon atoms, carbamoyl, alkylcarbamoyl of 2-7 carbon atoms, cycloalkylcarbamoyl of 4-11 carbon atoms, -CO₂Na, -CO₂K, alkoxycarbonyl of 2-7 carbon atoms, cycloalkoxycarbonyl of 4-11 carbon atoms, and aryloxycarbonyl of 7-13 carbon atoms. The one exception mentioned above is that when R is carbamoyl, R' can be, in addition, alkoxycarbonyl of 2-7 carbon atoms, cycloalkoxycarbonyl of 4-11 carbon atoms, or aryloxycarbonyl of 7-13 carbon atoms.

When $n=2$ in this embodiment R may be any of the radicals listed above for the condition of $n-1$ and R' is selected from the group consisting of di-t-alkylene of 6-20 carbon atoms, di-t-cycloalkylene of 6-20 carbon atoms, di-t-aralkylene of 12-20 carbon atoms, and

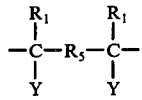

where R₁ and Y are as defined above and R₅ is alkylene of 1-10 carbon atoms or cycloalkylene of 3-10 carbon atoms. Furthermore, in this embodiment when $n=2$ and R is alkyl, cycloalkyl, aralkyl or

(as defined above with respect to the condition of $n=1$), R' can, in addition, be diacyl of 3-10 carbon atoms, diaroyl of 8-14 carbon atoms, arylene of 6-12 carbon atoms, or

where R₅ is alkylene of 1-10 carbon atoms, cycloalkylene of 3-10 carbon atoms, or alkyleneoxyalkylene of 2-20 carbon atoms.

When $n=3$ in this embodiment R may be any of the radicals listed above for the condition $n=1$ and R' is selected from the group consisting of tert-aralkyl-di-tert-aralkylene of 15-20 carbon atoms, tert-alkyl-di-tert-alkylene of 10-19 carbon atoms, trialkoxycarbonyl of 6-20 carbon atoms, triazinyl, triacyl of 6-20 carbon atoms, and triaroyl of 9-20 carbon atoms.

When $n=4$ in this embodiment R may be any of the radicals listed above for the condition $n=1$ and R' is selected from the group consisting of tetraacyl of 9-20 carbon atoms and tetraaroyl of 9-20 carbon atoms.

R and R¹, in any case, i.e., whether -X-X- is -O-O- or -N=N-, may contain additional substituents such as ester, amide, carbamate, carbonate, sulfonate, ether, and the like, which may or may not serve as the connecting link between R and/or R¹ and the ultraviolet absorbing group.

When $n$ is one, R and R¹ may be the same or different and when $n$ is greater than one, the R's may be the same or different and -XX- may be the same or different.

Specific radicals included within the generic descriptions given above for R and R¹ and the subgeneric descriptions for R₁, R₂, R₃, R₄, and R₄¹, are the following:

A. When -X-X- is -O-O- and $n=1$, R and/or R¹ may be 1. hydrogen (but only one of said R or R¹ may be hydrogen)
2. acyl which may be acyclic, cyclic, bicyclic, unsaturated, or substituted, such as acetyl, propionyl, pelargonyl, lauroyl, stearoyl, cyclohexanecarbonyl, norbornane-5-carbonyl, perhydronaphthalene-2-carbonyl, crotonyl, 3-butenoyl, 3-chloropropionyl, 4-ethoxycarbonylbutyryl; cinnamoyl;
3. aroyl which may be substituted or unsubstituted and includes 5- and 6-membered heterocyclics such as benzoyl, toluoyl, naphthoyl, p-phenylbenzoyl, p-chlorobenzoyl, p-methoxybenzoyl, p-nitrobenzoyl, o-carboxybenzoyl, p-phenylazobenzoyl, nicotinoyl, 2-furoyl;
4. tert-alkyl and tert-cycloalkyl such as t-butyl, t-amyl, 1,1,3,3-tetramethylbutyl, 1-methylcyclohexyl, 1-methylcyclodecyl, 2-cyclohexylisopropyl;
5. tert-aralkyl such as tert-cumyl, p-isopropylcumyl, 2-(2-naphthyl)isopropyl, t-(p-chlorocumyl);
6. alkoxycarbonyl such as methoxycarbonyl, propoxycarbonyl, isopropoxycarbonyl, 4-chlorobutoxycarbonyl, 2-ethylhexoxycarbonyl, tetradecyloxycarbonyl, hexadecyloxycarbonyl, octadecyloxycarbonyl, cyclohexyloxycarbonyl, cyclododecyloxycarbonyl, 1-perhydronaphthyloxycarbonyl;
7. carbamoyl, i.e.

8. alkyl or dialkyl carbamoyl of 2–13 carbon atoms such as dimethylcarbamoyl, ethylcarbamoyl, N-ethyl-N-cyclohexylcarbamoyl;

9. α-hydroxyalkyl such as α-hydroxyethyl, α-hydroxy-α-methylethyl, α-hydroxy-α-methylpropyl, α-hydroxy-α-ethyloctyl, 1-hydroxycyclohexyl, 1-hydroxycyclodecyl;

10. α-hydroperoxyalkyl such as α-hydroperoxyethyl, α-hydroperoxy-α-methylethyl, α-hydroperoxy-α-methylpropyl, α-hydroperoxy-α-ethyloctyl, 1-hydroperoxycyclohexyl, 1-hydroperoxycyclodecyl;

11. alkyl- and cycloalkylsulfonyl such as t-butylsulfonyl, t-amylsulfonyl, heptylsulfonyl, eicosylsulfonyl, cyclopentylsulfonyl, cyclohexylsulfonyl, methylcyclohexylsulfonyl, perhydronaphthylsulfonyl, 4-cyclohexylcyclohexylsulfonyl;

12. tert-alkoxyalkyl such as 2-methoxyisopropyl, 1-methoxy-1-methyloctadecyl, 1-methoxycyclohexyl, 1-ethoxycyclododecyl;

13. organomineral having the formula $(Q)_3M-$ or $(Q)_2M'-$ where M=silicon, germanium or tin, M' is boron, and Q=alkyl of 1–11 carbon atoms, phenyl, or benzyl such as trimethylsilyl, triphenylsilyl, triethylsilyl, tripropylgermanium, triphenylgermanium, trimethyltin, tricyclohexyltin, triphenyltin, dioctylboron, didecylboron, dicylodecylboron, dibenzylboron;

14. organophosphorus having the formula $$\underset{R_2P-}{\overset{O}{\|}}$$

or $$\underset{(RO)_2P-}{\overset{O}{\|}}$$

where R = alkyl of 1–8 carbon atoms or phenyl such as diethylphosphate, dimethylphosphate, diphenylphosphinic, di-n-octylphosphate, dibutylphosphinic.

B. When -X-X- is -O-O- and $n=2$, R can be any of the above radicals under group A and R' can be

1.

carbonyl 2. alkylidene or cycloalkylidene such as ethylidene, isopropylidene, pentylidene, 1-methylethylidene, 1-heptylpentylidene, 1-nonylheptylidene, cyclohexylidene, cyclododecylidene, cyclopropylidene;

3. organomineral having the formula $(Q)_2M=$ or $QM'=$ where Q, M, and M' are as defined above in A 13), such as dimethylsilyl, diphenylsilyl, diethylsilyl, dipropylgermanium, diphenylgermanium, dimethyltin, dicyclohexyltin, diphenyltin, octylboron, undecylboron, cyclodecylboron, benzylboron;

4. di-tert-alkylene or cycloalkylene such as tetramethylethylene, 1,1,4,4-tetramethyltetramethylene, 1,1,8,8-tetraethyloctomethylene, α,α,α',α'-tetramethyl-1,4-cyclohexenylenedimethylene;

5. di-tert-aralkylene such as α,α,α',α'-tetramethyl-p-phenylenedimethylene, α,α,α',α'-tetramethyl-p,p'-biphenylenedimethylene, α,α,α',α'-tetraethyl-1,4-naphthylenedimethylene;

C. When -X-X- is -O-O- and $n=3$, R can be any of the above radicals under group A and R' can be 1. tert-aralkyl-di-tert-aralkylene such as α,α,α',α',α''λ,α''-hexamethyl-s-phenenyltrimethylene, α,α,α',α'λ,α'',α''-hexaethyl-s-phenenyltrimethylene;

2. tert-alkylalkylidene, cycloalkylalkylidene, cycloalkylcycloalkylidene or alkylcycloalkylidene such as

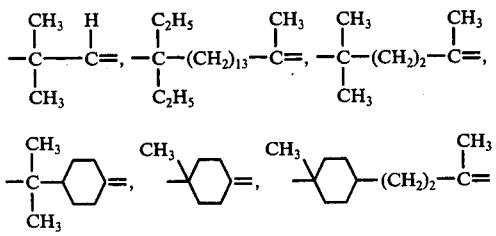

3. tert-alkyl-di-tert-alkylene such as

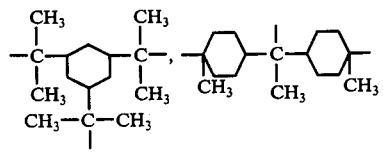

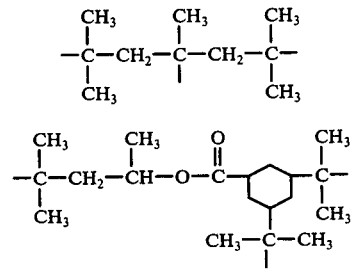

4. organomineral having the formula $QM\equiv$ where Q and M are as defined above in A —) such as methylsilyl, phenylsilyl, ethylsilyl, propylgermanium, phenylgermanium, methyltin, cyclohexyltin, phenyltin.

D. When -X-X- is -O-O- and $n=4$, R can be any of the above radicals under group A and R' can be 1. dialkylidene such as

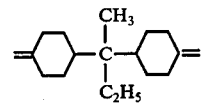

E. When -X-X- is -N=N- and $n=1$, R and R' may be 1. alkyl such as methyl, ethyl, isopropyl, t-butyl, t-amyl, t-octyl, eicosyl, 1,1-dimenthyldodecyl;

2. cycloalkyl such as cyclopropyl, cyclobutyl, 1-methylcyclopentyl, cyclohexyl, cyclooctyl, cyclodecyl;
3. aralkyl such as benzyl, phenethyl, t-cumyl, p-isopropyl-t-cumyl, p-phenyl-t-cumyl, 2-(2-naphthyl)isopropyl;
4.

which includes such radicals as

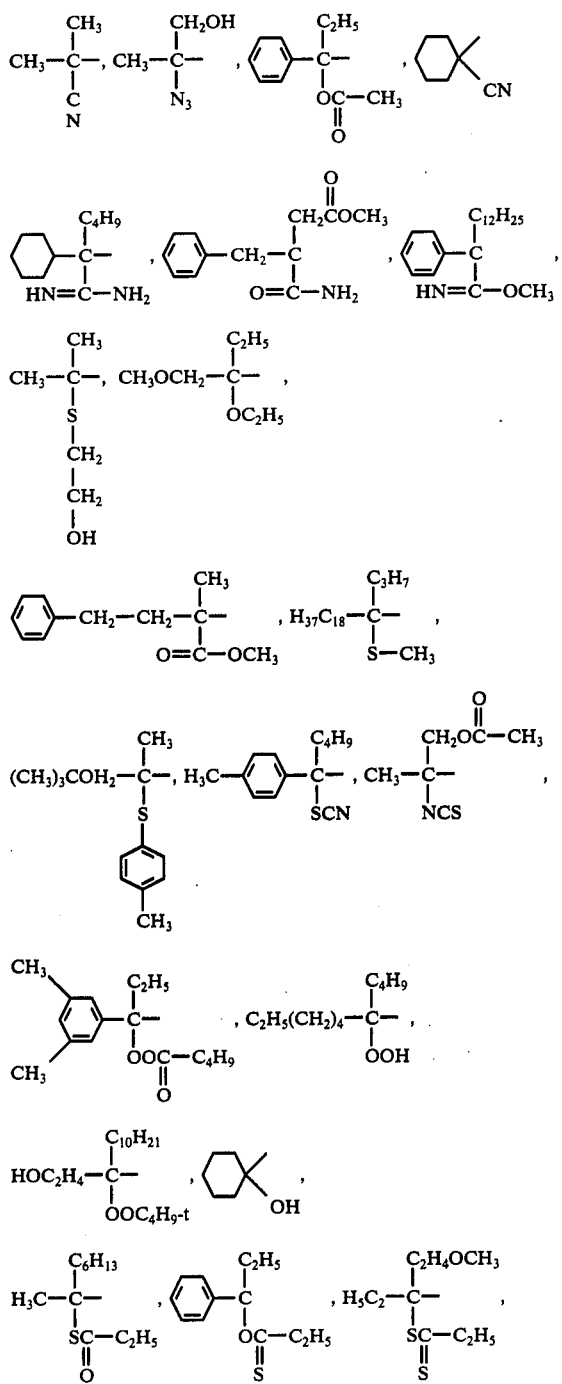

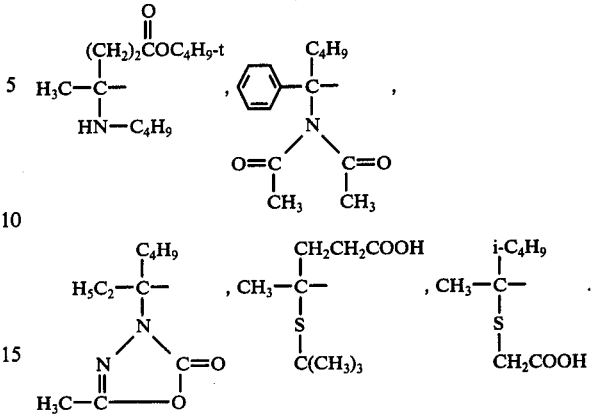

F. When -X-X- is -N=N- and $n=1$, one but not both of R and R' may be, in addition to those in E) above
1. aryl such as phenyl, tolyl, xylyl, naphthyl, p-phenylphenyl;
2. acyl such as those radicals listed above in A 2).
3. aroyl, such as those radicals listed above in A 3);
4. carbamoyl,

5. alkyl carbamoyl such as those radicals listed above in A 8);
6. -CO$_2$Na and -CO$_2$K
7. alkoxy-carbonyl and aryloxycarbonyl such as those radicals listed above in A 6) and phenyloxycarbonyl, tolyloxycarbonyl, xylyloxycarbonyl;

G. When -X-X- is -N=N-, $n=1$, and R is a carbamoyl group, R' can also be an alkoxycarbonyl or an aryloxycarbonyl as exemplified above in F 7).

H. When -X-X- is -N=N- and $n=2$, R can be any of the radicals above under E, F and G, and R' is
1. di-tert-alkylene and cycloalkylene such as those exemplifed above in B 4);
2. di-tert-aralkylene such as those exemplified above in B 5);
3.

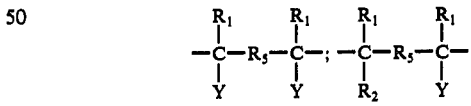

where $R_1$, $R_3$ and Y are as defined above and $R_5$ is alkylene or cycloalkylene such as methylene, ethylene, hexylene, decylene, cyclohexylene, oxydiethylene;

J. When -X-X- is -N=N- and $n=2$, R can be any definition under E above and R' can be, in addition to those mentioned in H
1. diacyl such as malonoyl, succinoyl, glutaroyl, sebacoyl;
2. diaroyl such as terephthaloyl, isophthaloyl, 4,4'-biphenylenedicarbonyl;
3. arylene such as p-phenylene, 4,4'-biphenylene, 1,4-naphthylene;
4.

such as 

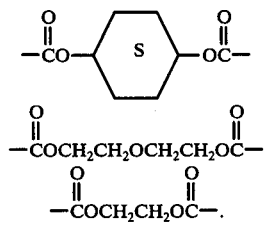

K. When -X-X- is -N=N- and n=3 R can be any radical defined under E above and R' can be:
1. tert.-aralkyl-di-tert.-aralkylene such as those exemplified in C1;
2. tert.-alkyl-di-tert.-alkylene such as those exemplified in C3;
3. trialoxycarbonyl such as

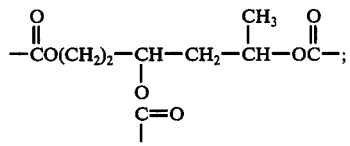

4. triazinyl

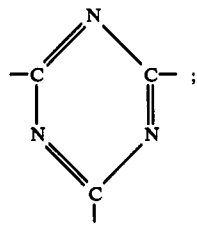

5. triacyl and triaroyl, such as

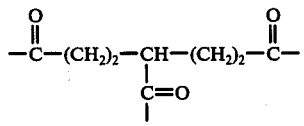

and

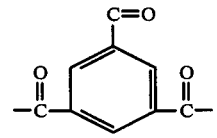

L. When —X—X— is -N=N- and $n=4$ R can be any radical defined under E above and R' can be tetraacyl ad tetraaroyl, such as

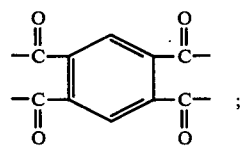

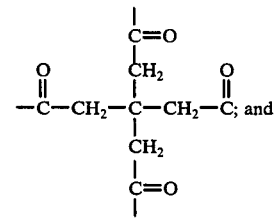

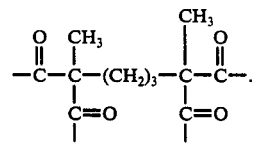

M. When $n$ is 2–4 and at least one of the -XX- groups is -O-O- and at least one of the -XX groups is -N=N-, the R connected to -OO- can be any radical listed under A above and the R connected to -N=N- can be any radical listed under E above and $R^1$ is a di-, tri-, or tetravalent radical composed of a combination of those radicals listed under A, B, and C for the -OO- linkage and those radicals listed under E, H, and K for the -N=N- linkage to $R^1$.

Some examples of such $R^1$ combinations are:

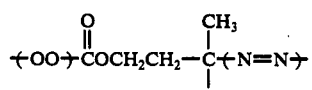  A + E combination

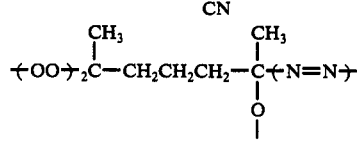  B + E combination

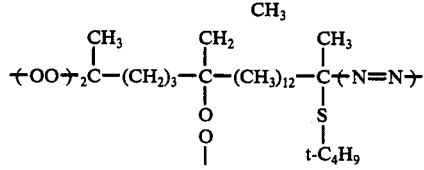  C + E combination

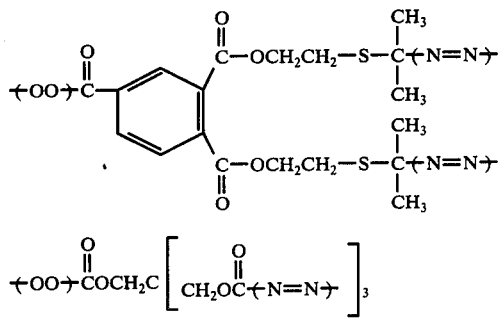

A + H combination

A + K combination

Compounds having aliphatic azo groups and peroxide groups in the same molecule and their preparation are disclosed in co-pending application Serial No. 37,310 entitled "Compounds having peroxy and aliphatic azo groups and methods using these as initiators".

In the foregoing descriptions, $R_1$ and $R_2$ are substituted or unsubstituted and are when not joined together alkyl of 1-20 carbon atoms or cycloalkyl of 3-6 carbon atoms. $R_1$ and $R_2$ when joined together form an alkylene of 2-30 carbon atoms. Typical examples of alkyl are methyl, ethyl, propyl, butyl, hexyl, decyl, dodecyl, octadecyl, and eicosyl. Typical examples of cycloalkyl are cyclopropyl, cyclobutyl, cyclopentyl and cyclohexyl. Typical examples of alkylene are ethylene, trimethylene, hexamthylene, octadecamethylene, tricosamethylene and triacontamethylene. $R_2$ is a tert.-alkyl of 4-8 carbon atoms, a tert.-cycloalkyl of 4-8 carbon atoms or a tert.- aralkyl of 9-15 carbon atoms. Typical examples of such are t-butyl, t-amyl, t-hexyl, t-heptyl, t-octyl, 1,1,3,3-tetramethylbutyl, 1-methylcyclohexyl, 2-cyclobutylisopropyl, t-cumyl, p-isopropylcumyl, 2-(2-naphtyl)- isopropyl, t-(p-chlorocumyl). $R_4$ and $R_4'$ are alkyl of 1-6 carbon atoms such as methyl, ethyl, propyl, hexyl, cycloalkyl of 3-6 carbon atoms, such as cyclopropyl, cyclobutyl, cyclopentyl, cyclohexyl; aryl of 6-12 carbon atoms such as phenyl, biphenyl, naphthyl, tolyl, xylyl; alkylene of 1-6 carbon atoms, such as ethylene, trimethylene, tetramethylene, hexamethylene; and arylene of 6-12 carbon atoms, such as phenylene, biphenylene, naphthylene.

$R_5$ is alkylene of 1-10 carbon atoms, such as methylene, ethylene, tetramethylene, hexamethylene, decamethylene, or cycloalkylene of 3-10 carbon atoms, such as cyclopropylene, cyclobutylene, cyclohexylene, cyclodecylene, 1,4-dimethylene- cyclohexane.

Ultraviolet light stabilizing compounds are well known, principally among those are phenyl salicylates, the orthohydroxy-benzophenones, the cyano-acrylates, and benzotriazoles. Particularly useful among these are the following compounds:

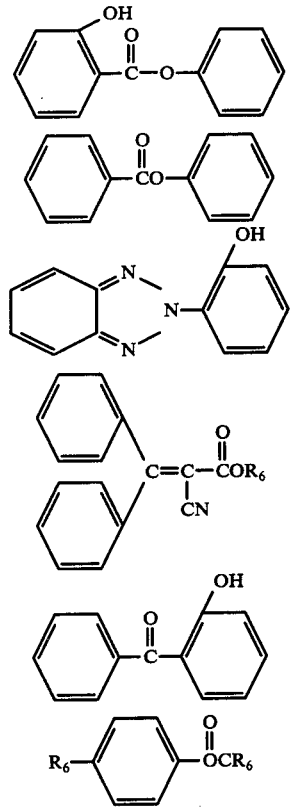

wherein $R_6$ is alkyl of 1-6 carbon atoms. These compounds are of course employed in the form of a radical in the compounds of the present invention so that they are joined to another moiety containing a peroxide grouping or an axo grouping. The location of the juncture in the ultraviolet light stabilizing group is at a ring carbon or a carbon atom in the $R_6$ group, usually through some coupling group such as an ester, amide, ether, sulfonate, carbonate, carbamate, etc.

Typical of the compounds of the present invention are the following:

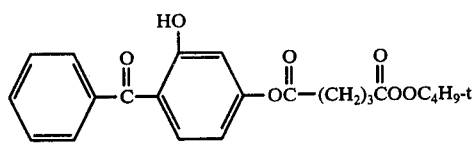

-continued
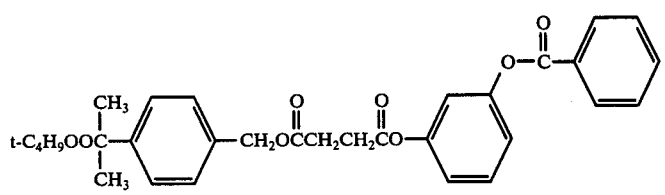
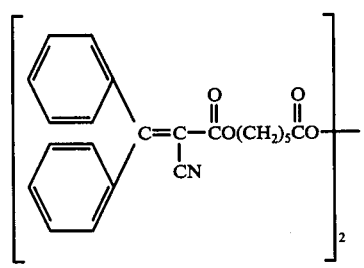
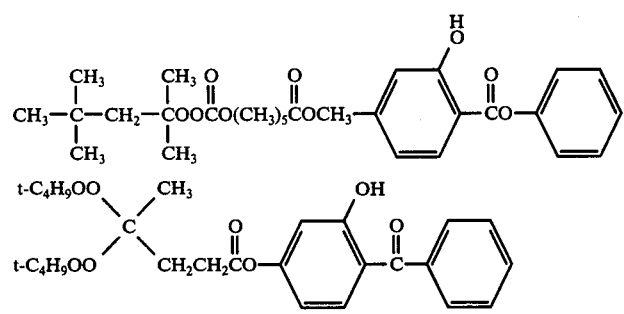
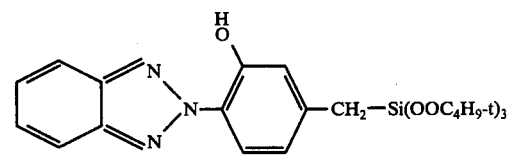
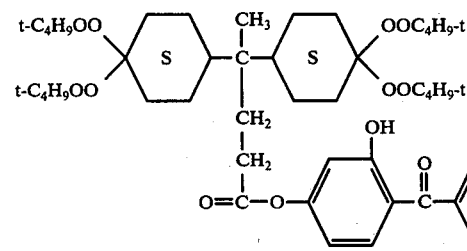
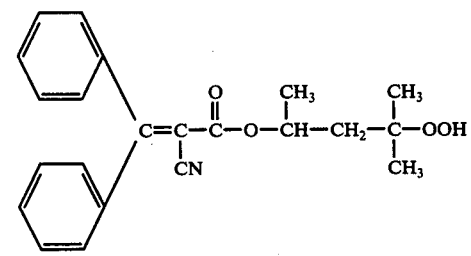
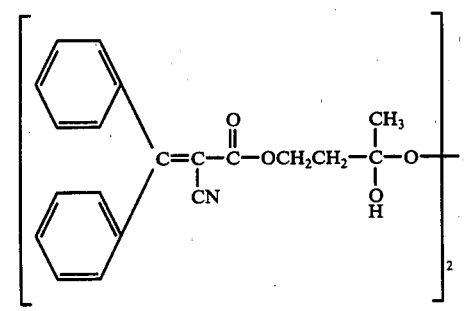

-continued
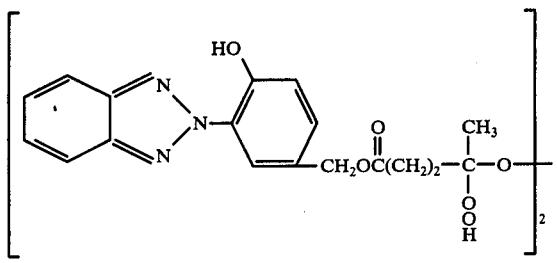
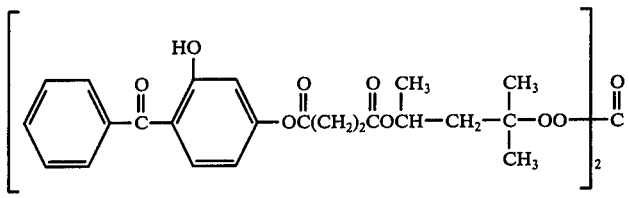
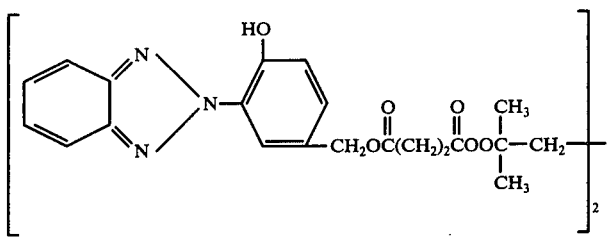
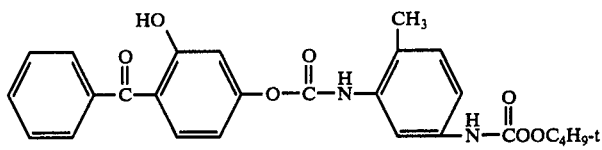
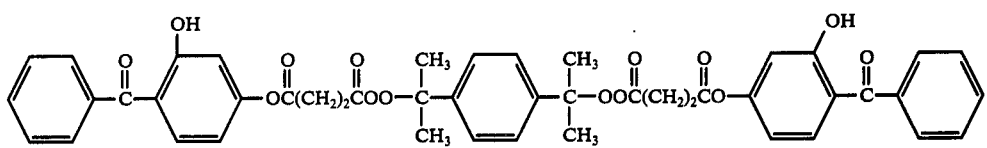
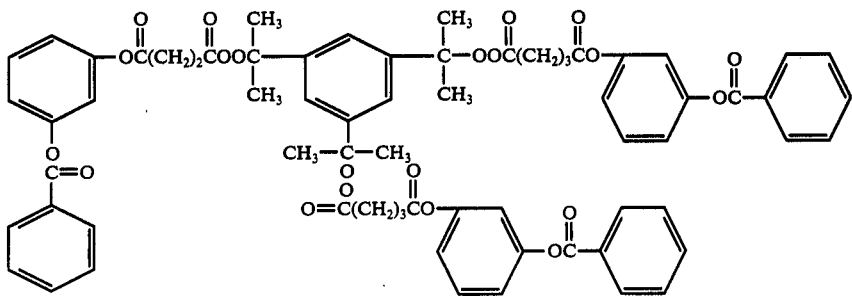
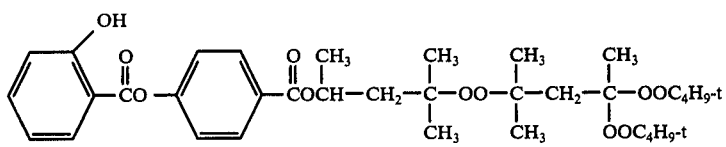
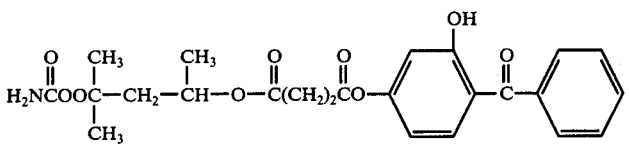

-continued
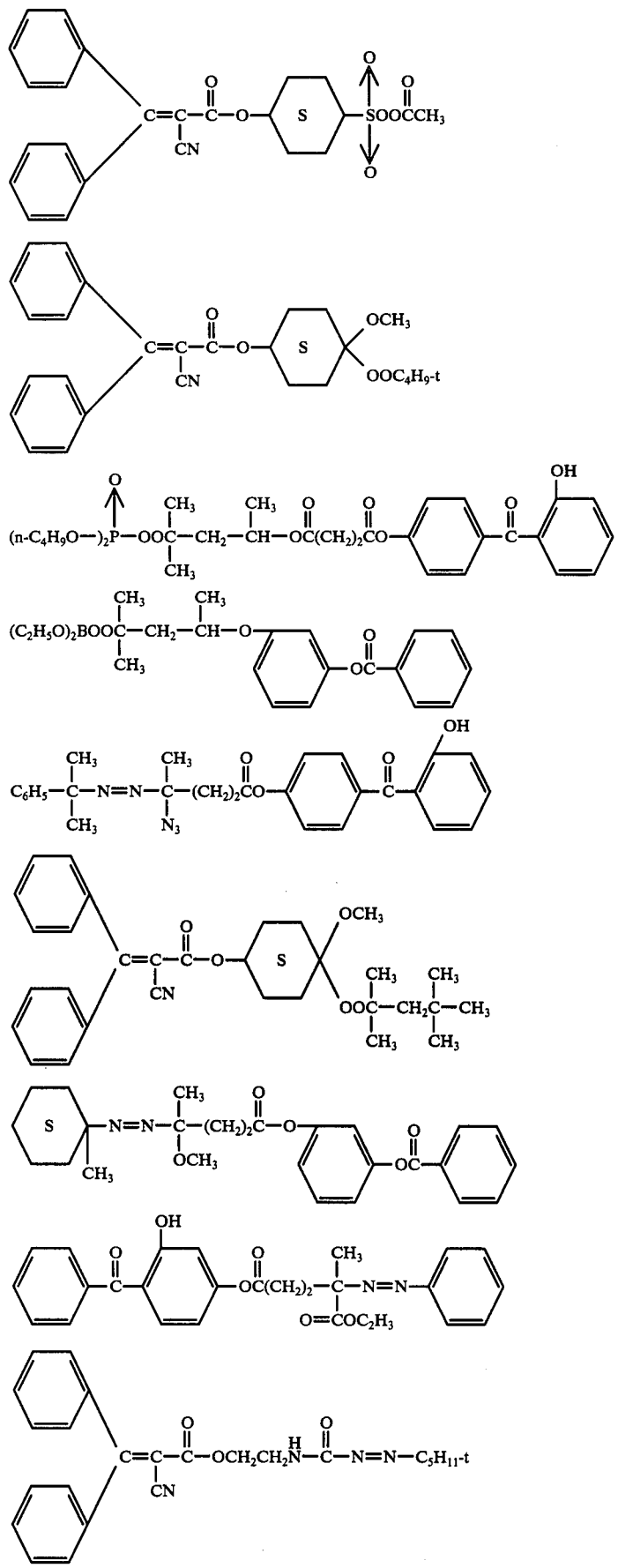

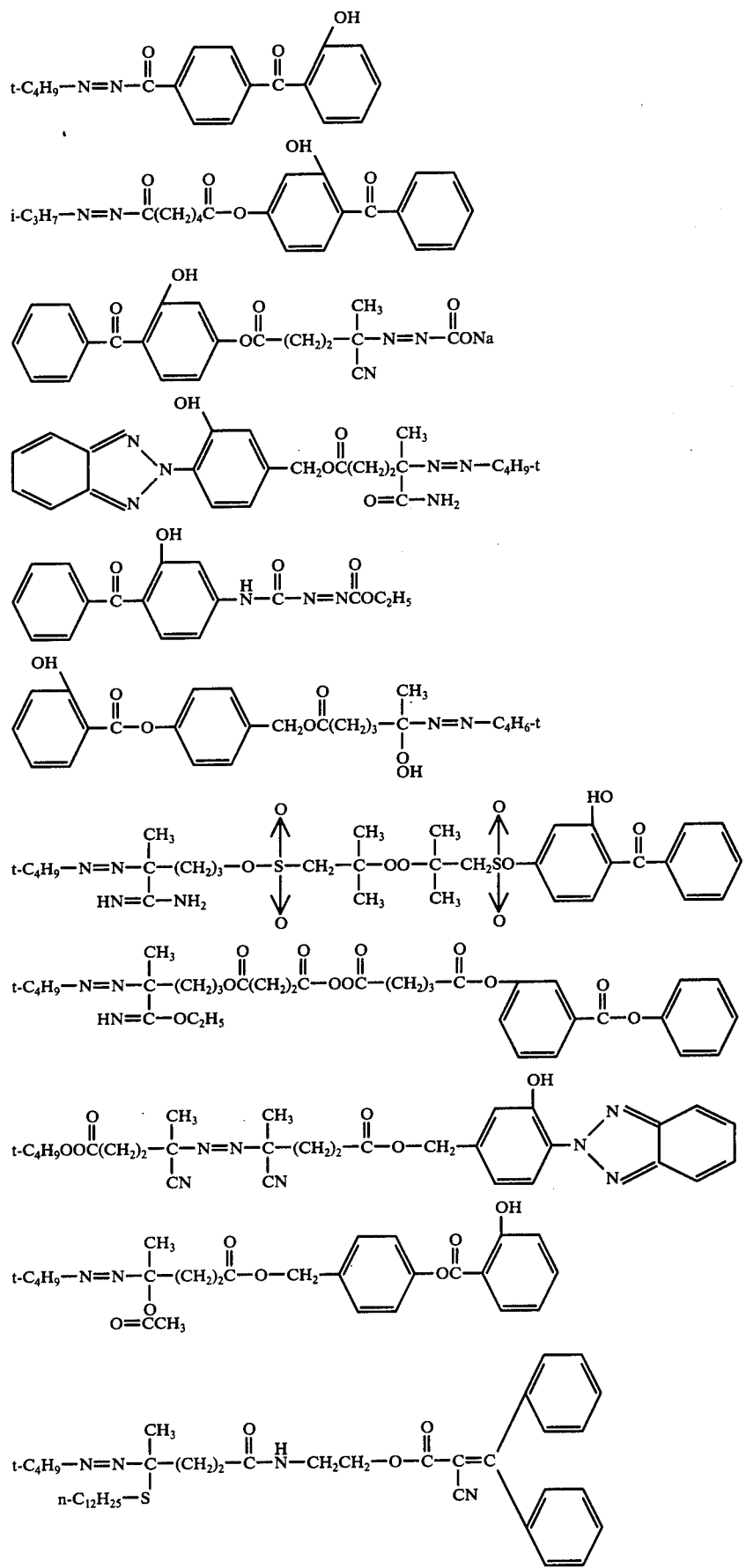

-continued
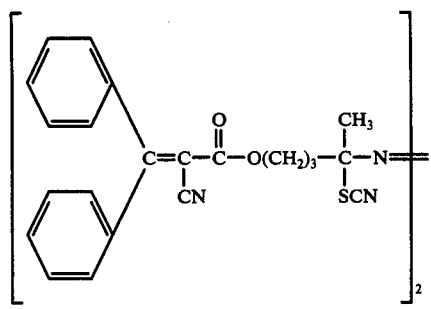
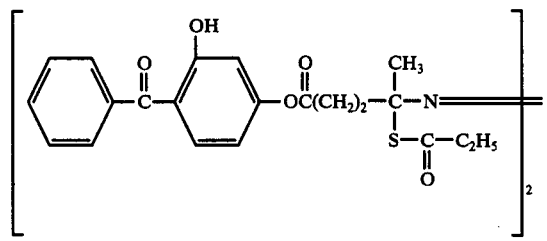
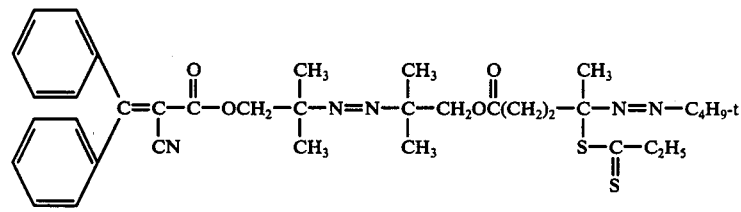
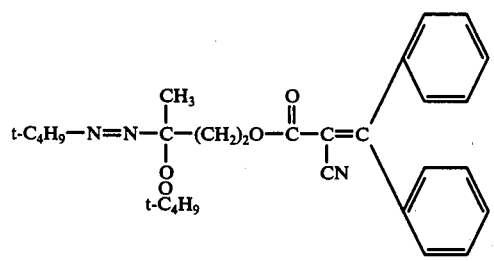
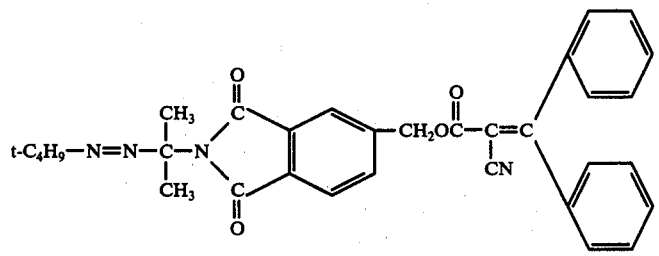
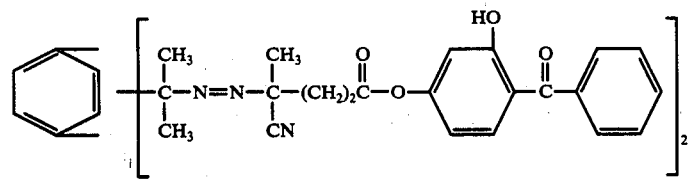
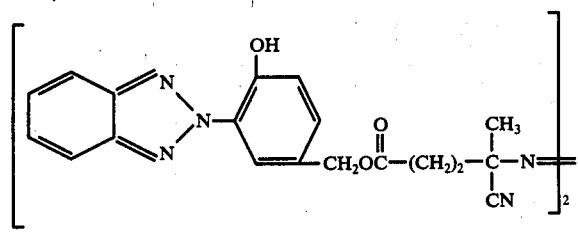

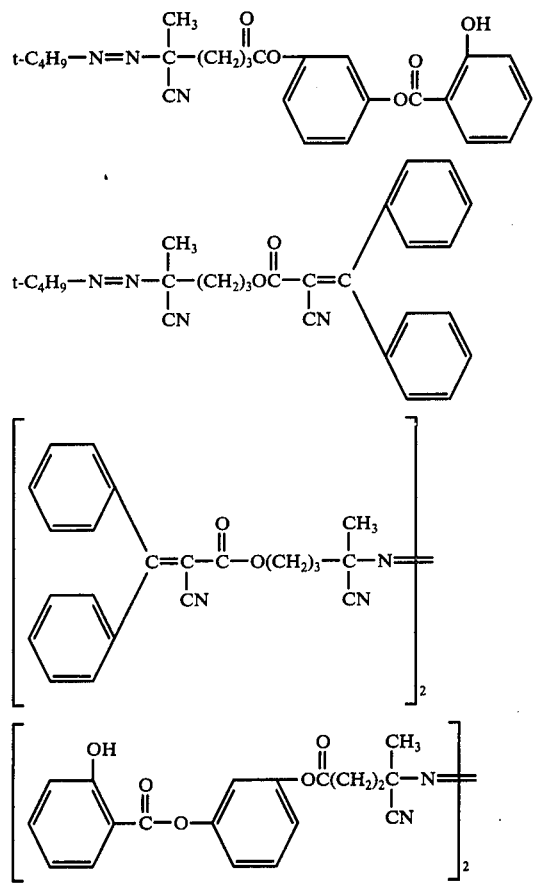

The requirements of a good UV stabilizer are that it must absorb strongly in the 300 to 400 millimicron range (preferably in the 300 - 370 range); exhibit long-term stability toward UV light; it must dissipate the solar energy in such a manner as to cause no degradation or color development in the plastic; it must impart little or no color to the plastic material at the normal-use level; it must be heat stable and chemically inert. In addition the UV stabilizer must have good compatibility with the particular polymer it is to be used with; have low volatility; and be relatively non-toxic.

Many UV absorbers fulfill the first set of requirements. The second set of requirements will also be fulfilled if the UV absorber is directly attached to the polymer chain as is the case with the polymers made by this invention. In addition to UV absorber will not leach out in the presence of solvents. The UV absorber will be uniformly dispersed throughout the polymer and it will not migrate to or away from the surface on standing.

In addition, the polymers prepared from these novel initiators contain from 1/2 to 2 ultraviolet stabilizing groups per polymer chain, in contrast to the copolymers derived from the ethylenically unsaturated derivatives of phenyl salicylate and 2-hydroxybenzophenone mentioned in the prior art. None of the problems normally encountered in a copolymerization such as the adjustment of monomer ratios with reactivity ratios of the monomers to get the desired composition of copolymer are encountered. In addition, many of the ethylenically unsaturated 2-hydroxybenzophenone and phenyl salicylate derivatives of the prior art tend to homopolymerize preferentially. Difficulties are also encountered when attempts are made to prepare homogeneous copolymers with monomers of lesser reactivity such as vinyl chloride and vinyl acetate. The ease with which many of these prior art UV stabilizers tend to polymerize also presents a problem with respect to their preparation, handling and storage.

In order to effectively withstand the effects of UV radiation the resultant polymers should contain at least 0.01% by weight of the initiating fragment containing the UV absorbing group. The maximum concentration will depend upon the particular monomer being polymerized and the specific end use of the polymer. In most cases a concentration of 2.0% of the UV absorbing fragment on the polymer will be the maximum concentration necessary unless the resultant polymer is to be used as a very thin coating, in which case more will be required, as much as 10% in some cases.

Although it is not possible to narrowly define an optimum concentration range because the exposure conditions of the polymers (such as degree of protection required, polymer thickness, etc.) vary considerably, a concentration range of 0.1 to 2.0% by weight will suffice for most applications. Each of the different polymers requires a certain concentration range of UV stabilizers for optimum protection because all of the polymers do not have the same susceptibility to degradation by UV. Table I shows some of the concentration ranges of UV absorber that are presently used for various polymers.

TABLE I

| Concentration Ranges for UV Stabilizers | |
|---|---|
| Polymer | Concentration, % (wt.) |
| polyacrylics | ≧0.01 |

TABLE I-continued

Concentration Ranges for UV Stabilizers

| Polymer | Concentration, % (wt.) |
| --- | --- |
| polyethylene | 0.01 - 1.0 |
| unsaturated polyesters | 0.1 - 2.0 |
| polystyrene | 0.2 - 0.5 |
| cellulosics | 0.2 - 2.0 |
| poly (vinyl chloride) | 0.25 - 1.0 |
| polypropylene | 0.5 - 2.0 |
| coatings | 0.1 - 5.0 |

The polymers of this invention may be prepared from the novel free radical polymerization initiators by any of the usual free radical polymerization techniques, i.e. bulk, suspension, solution, or emulsion polymerization techniques.

The polymerizations using these novel initiators may be carried out from below −20° C to above 200° C depending on the peroxide or azo structure of the initiator and the monomer employed. Generally the polymerizations will be carried out between 50° to 100° C depending on the half-life of the initiator used and the vinyl monomer being polymerized. Some free radical ethylene polymerizations are carried out above 200° C.

When initiators of the present invention are used to polymerize or copolymerize vinyl monomers, they first fragment into free radicals (equation 1) which then add to a vinyl monomer to form a new free radical (equation 2) which subsequently adds to more vinyl monomer and so on to form the growing polymer chain (equation 3):

1.

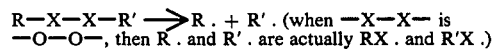

R—X—X—R' ⟶ R. + R'. (when —X—X— is —O—O—, then R. and R'. are actually RX. and R'X.)

2.

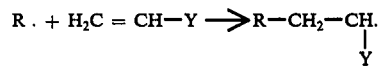

R. + H$_2$C = CH—Y ⟶ R—CH$_2$—CH.
                                  |
                                  Y

3.

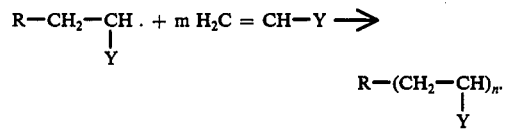

R—CH$_2$—CH. + m H$_2$C = CH—Y ⟶
      |
      Y

R—(CH$_2$—CH)$_n$.
         |
         Y

With some monomers, e.g. butadiene and styrene, the growing polymer chains terminate predominantly by coupling (equation 4) while with others the termination reaction may be by disproportionation of two growing polymer chains, hydrogen abstraction or chain transfer (e.g. equation 5):

4.

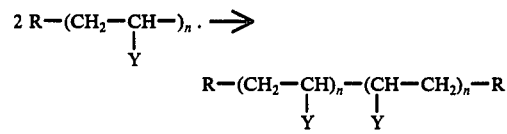

2 R—(CH$_2$—CH—)$_n$. ⟶
         |
         Y

R—(CH$_2$—CH)$_n$—(CH—CH$_2$)$_n$—R
         |            |
         Y            Y

5.

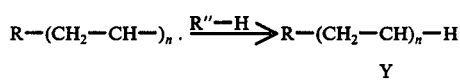

R—(CH$_2$—CH—)$_n$. $\xrightarrow{R''-H}$ R—(CH$_2$—CH)$_n$—H
         |
         Y Thus, it can be seen that when both R and R' contain UV stabilizing groups, i.e., when symmetrical initiators of the present invention are used each polymer chain will contain from one to two UV stabilizing groups, and that when only R contains a UV stabilizing group, i.e., when unsymmetrical initiators are used, only one half of the polymer chains will be initiated by a free radical containing a UV stabilizing group. In this case only one half of the polymer chains will contain UV stabilizing groups on the average.

Thus, one method of controlling the concentration of UV stabilizer in the polymer is the choice of using a symmetrical vs. unsymmetrical initiator of the present invention. This, of course, has to be correlated with the molar initiator requirements required in order to obtain the desired molecular weight of polymer at the desired temperature in the specified time period, which, in turn, varies with each monomer and comonomer system and is well known to the art.

Other methods of controlling the concentration of UV stabilizer in the polymer or copolymer is to use a conventional initiator in conjunction with the initiators of the present invention or to use initiators of the present invention of suitable molecular weight or to use initiators of the present invention that contain more than one ultraviolet absorbing group in both R and R'. The use of higher levels of initiators of the present invention can also be used but polymers of lower molecular weight are normally obtained when higher initiator levels are used. However, higher initiator levels can be used when carrying out the polymerization at lower temperatures without sacrificing molecular weight. Also, higher initiator levels are sometimes used to obtain shorter polymerization cycles. In any event, a variety of techniques can be employed to incorporate various levels of ultraviolet light stabilizing groups into the polymer or copolymer using the initiators of the present invention.

The novel free radical generators of the present invention can also be used to provide UV light stabilization to a variety of other materials which are prepared via processes requiring free radical generators. For example, they can be used as curing agents for resins such as alkyds and unsaturated polyester-vinyl monomer blends to provide the cured resins which are stabilized against UV light degradation. They can also be used as vulcanization agents for natural and synthetic rubbers and elastomers such as the silicone rubbers and the ethylene-propylene copolymers to provide vulcanized rubbers and elastomers which are stabilized against UV light degradation. They can also be used as crosslinking agents for various thermoplastic polymers and copolymers, such as polyethylene, polypropylene, ethylene-vinyl acetate copolymer, to provide the crosslinked polymers which are stabilized against UV light degradation. They can be used as the free radical sources for preparing block and graft copolymers to provide such copolymers which are stabilized against UV light degradation. Other uses for the novel free radical generators of the present invention to provide a source of free radicals and also impart stabilization toward UV light in the system will become apparent to those skilled in the art.

The novel free radical generators of this invention can be prepared by a variety of techniques such as:

1. reaction of a UV stabilizer having pendant OH, SH or NH groups (which are not necessary for UV absorption) with azos or peroxides containing acylating functions, as disclosed in copending application Ser. No. 667,352, filed Sept. 13, 1967, now abandoned, with respect to azos and as disclosed in copending applicatin Ser. No. 727,323, filed May 7, 1968, now U.S. Pat. No. 3,671,651, with respect to peroxides;

2. reaction of a UV stabilizer containing an acylating function wih an azo or peroxide containing a reactive OH, SH or NH group;

3. rearrangement of azos or peroxides containing phenyl esters of carboxylic acids. The rearrangement can take place either prior to using the free radical generator or as a post reaction, usually during the processing of the final product (polymer). This rearrangement is known as the Fries Reaction and can occur under thermal, photo, or Friedel Crafts conditions;

4. reaction of a UV stabilizer containing an active halogen (e.g. from a chloromethylation reaction) with an azo or peroxide containing a carboxylic acid salt; and 5. reaction of an azo or peroxide containing an active halogen with a UV stabilizer containing a carboxylic acid salt.

The evaluation of the novel initiators for their ability to produce UV stabilized polymers has been determined by polymerizing styrene using certain of the novel initiators and then determining the retention of flexural strength of the polystyrene upon exposure to UV light. The retention of flexural strength according to a modified ASTM Procedure D790-63 was compared with the retention of flexural strength of polystyrene prepared from azo an peroxide initiators of similar structure which did not have UV absorbing groups on them. Comparisons were also made with a polystyrene in which an extraneous UV absorber had been added after the polymerization was complete. Table II describes the polymerization initiator, the parts of the initiator per 100 hundred parts of monomer, the UV absorber present, the hours of exposure to UV radiation, the flexural strength and the percent flexural strength retained after UV exposure.

By comparing Runs 1-3 it is easy to see that the polystyrene prepared from the novel initiator 2-(4-t-butylazo- 4-cyanovaleryloxy)-2-hydroxybenzophenone had the greatest retention of flexural strength. The polystyrene which was prepared by adding an extraneous UV abosorber during the polymerization (Run 3) had intermediate stability with degradation occurring after 160 hours of UV radiation. The polystyrene without any UV stabilizer present (Run 2) had very poor stability, its flexural strength retention dropping to 57% after only 80 hours exposure.

By comparing Runs 4-6, it is again easy to see that the polystyrene prepared from the novel azo initiator (Run 4) had the greatest retention of flexural strength. In fact, the flexural strength actually increased on prolonged radiation. Again the polystyrene which was prepared by adding an extraneous UV absorber during the polymerization (Run 6) had intermediate stability. The polystyrene without any UV stabilizer present (Run 5) had very poor stability again.

By comparing Runs 9-11, it is obvious that the novel peroxide initiators are also quite effective in stabilizing polystyrene against UV radiation. Again the polystyrene prepared from the novel initiator (Run 9) had the greatest retention of flexural strength. The polystyrene which was prepared by adding an extraneous UV absorber during the polymerization (Run 11) had intermediate stability and the polystyrene without any UV stabilizer present (Run 10) had very poor stability.

It should be noted that the molecular weights of the polymers obtained in Runs 7, 8 and 12 in which the UV absorber was added on the mill are much lower than comparable samples in which no UV absorber was added. This indicates that polymer degradation was occurring on the mill. Therefore, this is not a very desirable method of incorporating a UV absorber into a polymer. Due to the polymer degradation on the mill, these polymers were not subjected to the UV radiation. Adding an extraneous UV absorber during a polymerization is not a very desirable method of incorporating a UV absorber into a polymer either, since this foreign substance can very often change the rate, and/or degree of polymerization as well as the molecular weight and physical properties of the finished polymer. It can also be partly or completely removed from the polymer in those instances where the polymer must be purified by washing and extraction techniques or during the removal of the medium used for the polymerization.

In the following examples, there are presented illustrative embodiments of this invention. Percentages and parts are by weight, and temperatures are in degrees centigrade unless otherwise noted.

EXAMPLE IA

Preparation of 4-(4-t-Butylazo-4-cyanovaleryloxy)-2-hydroxybenzophenone

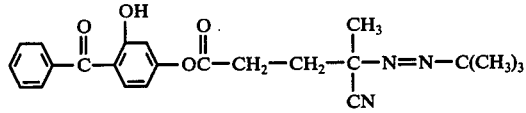

To a solution of 4.7 g. (.022 m) of 2,4-dihydroxybenzophenone and 2.5 ml. of pyridine in 35 ml. of ether in a 4 neck 100 ml. round bottom flask containing a thermometer, condenser and magnetic stirring bar was added 4.0 g. (.0218 m) of 4-t-butylazo-4-cyanovaleryl chloride dropwise with cooling so the temperature did not rise above 25° C. After completion of the addition the reaction mixture was stirred ½ hour at room temperature and then diluted with 100 ml. of water. The ether layer was separated, washed consecutively with 5% HCl, water, and 10% NaHCO₃ solution and saturated sodium chloride solution. The ether was evaporated off and the residue dissolved in methylene chloride, dried over anhydrous sodium sulfate, filtered and the methylene chloride stripped off under reduced pressure. The product weighted 8.8 g. (99% yield) and was a viscous syrup. The infrared spectrum was in agreement with the structure of the desired product.

PREPARATION OF 4-t-BUTYLAZO-4-CYANOVALERYL CHLORIDE

A. Preparation of 4-t-butylazo-4-cyanovaleric acid

To a mixture of 10.2 grams (.0876 mole) of levulinic acid in 25 ml of water was added in the following sequence: 7.04 grams (.0876 mole) of 50% sodium hydroxide, 5.88 grams (.12 mole) of sodium cyanide and 10.9 grams (.0438 mole) of t-butylhydrazine hydrochloride. The reaction mixture was stirred for 5 hours at room temperature, cooled to 5° C. and chlorine passed into the system holding the temperature below 15° C. until there was an increase in weight 10.0 grams (.14 mole). After the chlorination was over, the product was extracted with methylene chloride, the methylene chloride solution washed twice with water, dried over anhydrous sodium sulfate, filtered, and the methylene chloride evaporated on a rotating evaporator to leave 9.70 grams (52.5% yield) of crude product. The crude material was recrystallized from benzene-pentane to give 8.0 grams of product having a melting range of 79°-81° C.

B. Preparation of 4-t-butylazo-4-cyanovaleryl chloride.

Into a 25 ml round bottom flask was weighed 5 grams (.0237 mole) of 4-t-butylazo-4-cyanovaleric acid and then 15 ml of benzene and 2 ml of thionyl chloride were added. The acid dissolved and the solution was stirred for 4 hours at 25° C ± 2° C (protected from the atmosphere by a CaCl₂ tube). At the end of the stirring period the benzene and excess thionyl chloride were evaporated under reduced pressure leaving 5.35 grams (98.8% yield) of 4-t-butylazo-4-cyanovaleryl chloride.

EXAMPLE IB

Curing an Unsaturated Polyester-Styrene Resin with 4-(4-t-butylazo-4-cyanovaleryloxy)-2-hydroxybenzophenone An unsaturated polyester resin was prepared by reacting maleic anhydride (1.0 mole), phthalic anhydride (1.0 mole), and propylene glycol (2.2 moles) until an acid number of 45-50 was obtained. To this was added hydroquinone at a 0.013% concentration. Seven parts of this unsaturated polyester was diluted with 3 parts of monomeric styrene to obtain a homogeneous blend having a viscosity of 13.08 poise and a specific gravity of 1.14.

To 20 grams of this blend was added 0.2 gram of 4-(4-t-butylazo-4-cyanovaleryloxy)-2-hydroxybenzophenone and the resultant composition placed in a constant temperature bath at 212° F. The internal temperature was recorded as a function of time and a peak exotherm of 422° F was reached in 6.6 minutes indicating an excellent cure of the unsaturated polyester-styrene resin blend had occurred. Without an initiator, no cure of this resin blend occurred after more than 30 minutes at 212° F.

EXAMPLE II

Preparation of 4,4'-Di(4-t-butylazo-4-cyanovaleryloxy)-2-hydroxybenzophenone

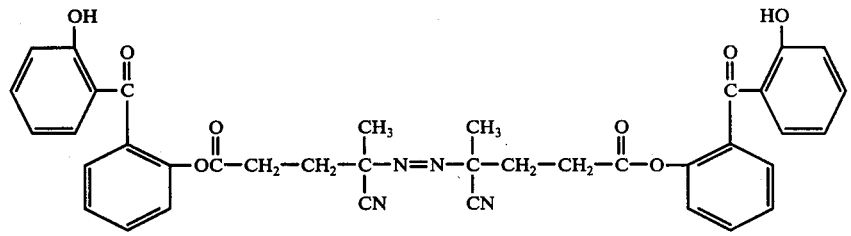

To a solution of 2.04 g. (.0085 m) of 2,4,4'-trihydrox-

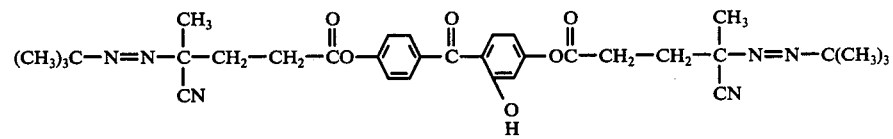

ybenzophenone and 2.5 ml of pyridine in 30 ml of ether in a 4 neck 100 ml round bottom flask equipped with a thermometer, condenser and magnetic stirring bar was added 3.9 g. (.017 m) of 4-t-butylazo-4-cyanovaleryl chloride dropwise with cooling so the temperature did not rise above 25° C. After completion of the addition the reaction mixture was stirred ½ hour at room temperature and then diluted with 100 ml of water. The ether layer was separated, washed consecutively with 5% HCl, water, 10% NaHCO₃ solution and saturated sodium chloride solution. The ether was evaporated off and the residue dissolved in methylene chloride, dried over anhydrous sodium sulfate, filtered and the methylene chloride stripped off under reduced pressure. The product weighed 4.0 g. (77% yield) and was a viscous syrup. The infrared spectrum of the product was in agreement with the structure of the desired product.

EXAMPLE III

Preparation of 2-(4-t-butylazo-4-cyanovaleryloxy)-2°-hydroxybenzophenone

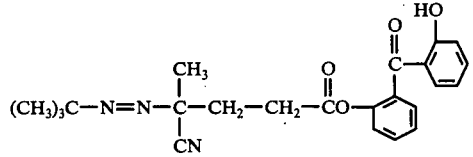

To a solution of 4.68 g. (.0218 m) of 2,2'-dihydroxybenzophenone and 2.5 ml of pyridine in 30 ml of ether in a 4 neck 100 ml round bottom flask equipped with a termometer, condenser and magnetic stirring bar was added 5.0 g. (0.0218 m) of 4-t-butylazo-4-cyanovaleryl chloride dropwise with cooling so the temperature did not rise above 25° C. After completion of the addition the reaction mixture was stirred ½ hour at room temperature and then diluted with 100 ml of water. The ether layer was separated, washed consecutively with 5% HCl, water, 10% NaHCO₃ solution and saturated sodium chloride solution. The ether was evaporated off leaving a yellow solid. The solid was slurried in pentane, filtered and air dried. The product weighed 6.3 g. (71.2% yield) and decomposed slowly on heating above 80° C. The infrared spectrum of the product was in agreement with the structure of the desired product.

EXAMPLE IV

Preparation of Di-[2-(2-hydroxybenzoyl)phenyl] trans-4,4'-azobis(4-cyanovalerate)

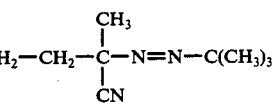

To a solution of 7.05 g. (.0328 m) of 2,2'-dihydroxybenzophenone and 3.5 ml. of pyridine in 50 ml. of benzene in a 4 neck 100 ml round bottom flask equipped with a thermometer, condenser and magnetic stirring bar was added 5.2 g. (.0164 m) of trans-4,4'-azobis(4-cyanovaleryl chloride) as a solid in small increments with cooling so the temperature did not rise above 25° C. After completion of the addition the reaction mixture was stirred 2 hours at room temperature and then diluted with 100 ml. of water. The benzene layer was separated and washed with 5% HCl and water. It was dried over anhydrous sodium sulfate, filtered and the benzene stripped off. The product was a viscous syrup and weighed 8.4 g. (76% yield). The infrared spectrum of the product was in agreement with the structure of the desired product.

PREPARATION OF

TRANS-4,4'-AZOBIS(4-CYANOVALERYL CHLORIDES)

A. Preparation of Cis- and Trans-4,4'-Azobis(4-cyanovaleric acid)

A solution of 154.8 grams (1.82 moles) levulinic acid, 53.2 grams (1.32 moles) sodium hydroxide and 21.8 grams (0.66 mole) of 97% hydrazine was refluxed in an oil bath for 5 hours. The solution was cooled to room temperature, 160 ml HCN added, and the reaction stirred overnight. The solution was then made acid with a few ml of conc. HCl and the excess HCN was stripped off under aspirator vacuum, trapping the volatile HCN in a "Dry Ice" trap. After most of the excess HCN had been stripped off, the solution was made basic again with 50% NaOH and chlorine passed into the system. The temperature was controlled below 15° C by means of an ice bath and the chlorine passed in until the exotherm ceased (approximately 85 grams or 1.2 moles). During the oxidation, a solid precipitated out of solution. The solid was filtered off, washed once with cold water and air dried. The crude yield was 140 grams (76% yield) of a light brown powder having a melting range of 118°–125° C. Repeated recystallization from ethyl alcohol and ethyl acetate separated the product into two pure isomeric forms, one melting at 141°–143° C (35 grams from ethanol) and the other at 125°–127° C (22.5 grams from ethyl acetate). The higher melting isomer was also the less soluble isomer and was assigned the trans-structure, and the other isomer was assigned the cis-structure.

B. Preparation of Trans-4,4'-azobis(4-cyanovaleryl chloride)

A mixture of 10 grams (.0358 mole) trans-4,4'-azobis (4-cyanovaleric acid) and 200 ml of thionyl chloride in a 500 ml round bottom flask containing a magnetic stirring bar and a condenser with a drying tube, was refluxed for 1 hour in a 100° C oil bath. The resulting solution was filtered while still warm and the excess thionyl chloride stripped from the filtrate. The residue was slurried in benzene and stripped to dryness. The resultant solid was dissolved in warm benzene, filtered and precipitated back out with pentane. The solid was filtered off and dried. The yield was 5.4 grams (47.5% yield) of a white powder with a melting range of 81°–83° C. (dec.).

EXAMPLE V

Preparation of Di-(3-hydroxy-4-benzoylphenyl)trans-4,4'-azobis(4-cyanovalerate)

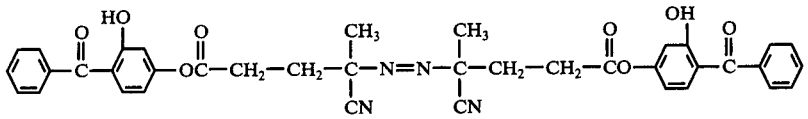

To a solution of 10.7 g. (.050 m) of 2,4-dihydroxybenzophenone and 4.5 ml. of pyridine in 70 ml. of methylene chloride in a 200 ml. 4-neck round bottom flask equipped with a thermometer, condenser and magnetic stirring bar was added 7.9 g. (.025 m) of trans-4,4'-azobis(4-cyanovaleryl chloride) as a solid in small increments with cooling so the temperature did not rise above 25° C. After completion of the addition the reaction mixture was diluted with 150 ml. water and the methylene chloride layer separated. The organic layer was washed with 5% HCl and water, dried over anhydrous sodium sulfate, filtered and the methylene chloride stripped off. The residue was a light tan tacky solid weighing 15.2 g. (90.5% yield). The infrared spectrum of the product was in agreement with the structure of the desired product.

EXAMPLE VI

Preparation of Di-[2-(2-hydroxybenzoyl)phenyl] cis-4,4'-azobis(4-cyanovalerate)

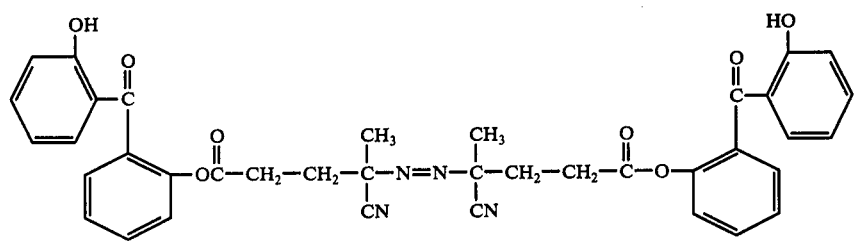

To a solution of 12.5 g. (.0583 m) of 2,2'-dihydroxybenzophenone and 6 ml. of pyridine in 75 ml. of benzene in a 4 neck 200 ml. round bottom flask equipped with a thermometer, condenser and magnetic stirring bar was added 9.2 g. (.0291 m) of cis-4,4'-azobis(4-cyanovaleryl chloride), as a solid in small increments, with cooling so the temperature did not rise above 35° C. After completion of the addition, the reaction mixture was stirred 2½ hours at room temperature and then diluted with 100 ml. water. The benzene layer was separated and washed with 5% HCl and then with water until neutral. The benzene solution was dried over anhydrous sodium sulfate, filtered and the benzene stripped off. The residue was a light yellow tacky solid weighing 20.5 g. (105% yield). The infrared spectrum showed the product was in agreement with the structure of the desired product and that a small amount of benzene was still present in the tacky solid.

Preparation of Cis-4,4'-Azobis(4-cyanovaleryl chloride)

A 500 ml. 3-neck flask containing 20.7 grams (.074 mole) of cis-4,4'-azobis(4-cyanovaleric acid) (prepared as described in Example IV), 120 ml. thionyl chloride, a magnetic stirring bar, a thermometer, and a condenser with a drying tube was immersed into an oil bath preheated to 125° C. At the end of 8 minutes complete solution was obtained and the oil bath was rapidly replaced by an ice bath. The solution was cooled to room temperature and the excess thionyl chloride stripped off. The residue was slurried in benzene and the benzene stripped off. The resulting solid was dissolved in warm benzene and then precipitated by the addition of pentane. The precipitate was filtered off and dried. The yield was 20.7 grams (88.4% yield) of a white powder with a melting range of 88°-90° C. (dec.).

EXAMPLE VII

Preparation of OO-t-butyl 0-2(2-hydroxybenzoyl) phenyl monoperoxyphthalate

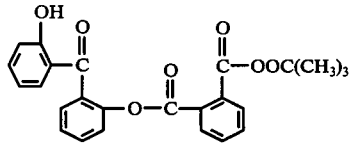

To a solution of 10.7 g. (.05 m) of 2,2'-dihydroxybenzophenone and 4.9 ml of pyridine in 50 ml. of methylene chloride in a 4 neck 100 ml. round bottom flask equipped with a thermometer condenser and magnetic stirring bar was added 12.8 g. (.05 m) of t-butyl peroxy-2-(chloro-carbonyl) benzoate dropwise over ½ hour holding the temperature between 20-25° C with a cold water bath. After the addition was complete, the reaction mixture was stirred an additional 1 hour at room temperature. The reaction mixture was then diluted with 100 ml of water, the methylene chloride layer separated and washed consecutively with 5% HCl, water, 10% NaHCO₃ solution and saturated sodium chloride solution, dried over anhydrous sodium sulfate, filtered and the methylene chloride stripped off. The residue weighed 20.5 g. (94.3% yield) and assayed 85.6%. The infrared spectrum of the product was in agreement with the structure of the desired product.

Preparation of t-Butylperoxy 2-(Chlorocarbonyl)benzoate

To a suspension of 22.9 grams (0.096 mole) OO-t-butyl hydrogen monoperoxyphthalate in 150 ml. of benzene at 10° C. was added 20.0 grams (.096 mole) of PCl₅ in a single portion. The components went into solution, the ice bath was removed and the temperature was allowed to rise to room temperature. At the end of 1¾ hours stirring time, the reaction mixture was stirred into 150 ml. of ice water, stirred 3 minutes, the organic layer separated, dried over anhydrous sodium sulfate, filtered and the benzene evaporated under reduced pressure to give 23.5 grams (95.7% yield) of crude product. This general process is described in copending patent application Ser. No. 727,323, filed May 7, 1968.

EXAMPLE VIII

General Procedure for Evaluation of UV Light Stability of Polystyrene Prepared from Novel Initiators The polystyrene was prepared by a suspension polymerization technique using 1,000 grams of water, 0.0828 grams of gelatin, 50 grams of calcium phosphate, 500 grams of styrene and the amount of initiator indicated in Table II. In some cases, 2-acetoxy-2'-hydroxybenzophenone, a UV absorber of similar structure to that in the novel initiators used, was added during the polymerization step or after the polymerization on a rubber mill. In all cases, with the exception of the blanks, the concentration of the UV absorbing structure was kept at 0.5 parts per hundred of styrene monomer. The polymerizations were carried out between 75° - 95° C depending on the half-life of the initiator. In any event, the controls were run through the same heating cycle as the comparative polymerizations.

The polystyrene was press molded at 300° F for 5 minutes into 5 inches X ½ inch X ¼ inch bars. These bars, four to a set, were then exposed to a Westinghouse 275 Watt sunlight bulb for 0, 80, 160 and 240 hours according to a modified ASTM Procedure D620-57T. After the exposure periods, flexural strengths of the polystyrene prepared from the various initiator systems were determined according to ASTM Procedure D790-63. The results are tabulated in Table II.

TABLE II

| Run # | Polymerization Initiatior | M.W. | PHR | U.V. Absorber | PHR of U.V. Absorber | Exposure to U.V. Radiation (Hrs.) | Flexural Strength (PSI) | % Flexural Strength Retained | Molecular Weight of Polymer |
|---|---|---|---|---|---|---|---|---|---|
| 1 | 2-(4-t-Butyiazo-4-cyanovaleryloxy-2'hydroxybenzophenone (From Example IA) | 407 | 0.755 | Attached | 0.5 | 0 | 7243 | — | 302,800 |
|   |   |   |   |   |   | 80 | 6384 | 88.1 |   |
|   |   |   |   |   |   | 160 | 6595 | 91.1 |   |
|   |   |   |   |   |   | 240 | 6581 | 90.9 |   |
| 2 | Ethyl 4-t-Butyiazo-4-cyanovalerate | 239 | 0.443 | None | 0 | 0 | 8708 | — | 327,000 |
|   |   |   |   |   |   | 80 | 4805 | 57.2 |   |
|   |   |   |   |   |   | 160 | 5088 | 58.4 |   |
|   |   |   |   |   |   | 240 | 4020 | 46.2 |   |
| 3 | Ethyl 4-t-Butyinzo-4-cyanovaicrate | 239 | 0.443 | 2-Acetoxy-2'-hydroxybenzophenone (added during Polymerization) | 0.5 | 0 | 6830 | — | 333,000 |
|   |   |   |   |   |   | 80 | 6328 | 92.7 |   |
|   |   |   |   |   |   | 160 | 6565 | 96.1 |   |
|   |   |   |   |   |   | 240 | 5053 | 74.0 |   |
| 4 | Di-2-(2-hydroxybenzoyl)phenyl cis-4,4'-Azobis(4-cyanovalerate) (From Example VI) | 672 | 0.624 | Attached | 0.5 | 0 | 5188 | — |   |
|   |   |   |   |   |   | 80 | 5100 | 98.3 |   |
|   |   |   |   |   |   | 160 | 5658 | 109.0 |   |
|   |   |   |   |   |   | 240 | 5615 | 108.2 |   |
| 5 | Azobisisobutyronitrile | 164 | 0.344 | None | 0 | 0 | 7626 | — | 314,500 |
|   |   |   |   |   |   | 80 | 6387 | 83.8 |   |
|   |   |   |   |   |   | 160 | 5715 | 74.9 |   |
|   |   |   |   |   |   | 240 | 3994 | 52.4 |   |
| 6 | Azobisisobutyronitrile | 164 | 0.344 | 2-Acetoxy-2'- | 0.5 | 0 | 7173 | — | 308,000 |

TABLE II-continued

| Run # | Polymerization Initiator | M.W. | PHR | U.V. Absorber | PHR of U.V. Absorber | Exposure to U.V. Radiation (Hrs.) | Flexural Strength (PSI) | % Flexural Strength Retained | Molecular Weight of Polymer |
|---|---|---|---|---|---|---|---|---|---|
| | | | | hydroxybenzophenone (added during Polymerization) | | 80 | 6340 | 88.4 | |
| | | | | | | 160 | 6750 | 94.1 | |
| | | | | | | 240 | 6498 | 90.6 | |
| 7 | Ethyl 4-t-Butylazo-4-cyanovalerate | 239 | 0.443 | 2-Acetoxy-2'-hydroxybenzophenone (added on mill) | 0.5 | 0 | 6678 | — | 222,000 |
| 8 | Azobisisobutyronitrile | 164 | 0.344 | 2-Acetoxy-2'-hydroxybenzophenone (added on mill) | 0.5 | 0 | 6600 | — | 167,800 |
| 9 | OO-t-Butyl O-2-2-Hydroxybenzoyl)-phenyl Monoperoxyphthalate (From Example VII) | 434 | 0.805 | Attached | 0.5 | 0 | 11023 | — | 248,000 |
| | | | | | | 80 | 10733 | 97.2 | |
| | | | | | | 160 | 9695 | 87.2 | |
| | | | | | | 240 | 9783 | 87.7 | |
| 10 | OO-t-Butyl O-Ethyl Monoperoxyphthalate | 266 | 0.492 | None | 0 | 0 | 11830 | — | 248,000 |
| | | | | | | 80 | 8595 | 72.6 | |
| | | | | | | 160 | 7556 | 64.8 | |
| | | | | | | 240 | 5721 | 48.4 | |
| 11 | OO-t-Butyl O-Ethyl phthalate Monoperoxyphhatate | 266 | 0.492 | 2-Acetoxy-2'-hydroxybenzophenone (added during Polymerization) | 0.5 | 0 | 8814 | — | 213,000 |
| | | | | | | 80 | 8578 | 97.3 | |
| | | | | | | 160 | 7201 | 81.8 | |
| | | | | | | 240 | 7200 | 81.8 | |
| 12 | OO-t-Butyl O-Ethyl monoperoxyphthalate | 266 | 0.492 | 2-Acetoxy-2'-hydroxybenzophenone (added on mill) | 0.5 | 0 | 8691 | — | 174,000 |

EXAMPLE IX

Preparation of OO-t-Butyl- O-p-Tolyl Monoperoxysuccinate

To a vigorously stirred solution of 15.6 g. (0.143 mole) of 82.0% t-butyl hydroperoxide and 57.0 g. (0.143 mole) of aqueous 10% sodium hydroxide at 5°-10° C was added slowly 24.6 g. (0.109 mole) of 3-(p-tolyoxycarbonyl)propionyl chloride (prepared from p-tolyl 3-carboxypropionate and thionyl chloride) in 50 ml. of diethyl ether. The reaction mixture was then stirred at 5°-10° C for 3 hours, after which additional ether was added to the mixture and the resulting ether solution was washed, first with 10% sodium hydroxide solution, and finally with water until the solution was neutral. After drying over anhydrous MgSO₄ and removal of the ether in vacuo 28.2 g. (theory, 30.4 g.) of white solid, m.p. 72°-77° C, was obtained. The assay according to "active oxygen" content was 100% and the corrected yield was 92.8%.

EXAMPLE X

Preparation of OO-t-Butyl O-p-Tolyl Monoperoxyglutarate

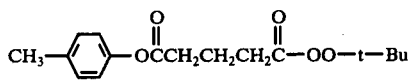

To a vigorously stirred solution of 4.9 g. (0.045 mole) of 82.0% t-butyl hydroperoxide and 18.0 g. (0.045 mole) of aqueous 10% sodium hydroxide at 10°-14° C was slowly added 8.2 g. (0.034 mole) of 4-(p-tolyloxycarbonyl)butyryl chloride (prepared from p-tolyl 4-carboxybutyrate and thionyl chloride) in 25 ml. of diethyl ether. The reaction mixture was then stirred for 3.5 hours at 8°-10° C. After a work-up similar to that in Example I 8.2 g. (theory, 10.0 g.) of white solid, m.p. 50°-55° C, was obtained. The assay according to "active oxygen" content was 93.6% and the corrected yield was 76.7%.

EXAMPLE XI

Preparation of Di-[3-(p-tolyloxycarbonyl)propionyl] Peroxide

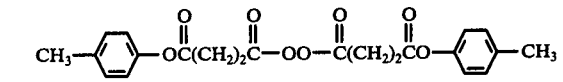

To a vigorously stirred solution of 2.0 g. (0.029 mole) of 50% H₂O₂ and 25.2 g. (0.063 mole) of aqueous 10% sodium hydroxide at 10°-14° C was added slowly 10.9 g. (0.0483 mole) of 3-(p-tolyloxycarbonyl)propionyl chloride in ether solution. The resulting reaction mixture was stirred for an additional three hours. After a work-up similar to that in Example I 9.1 g. (theory, 10.0 g.) of white solid, m.p. 94°-106° C (decomp.) was obtained. The assay according to "active oxygen" content was 92.3% and the corrected yield was 83.9%.

EXAMPLE XII

Preparation of Di-[4-(p-tolyloxycarbonyl)butyryl] Peroxide

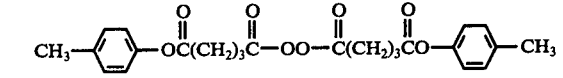

To a vigorously stirred solution of 1.7 g. (0.025 mole) of 50% hydrogen peroxide and 22.7 g. (0.057 mole) of aqueous 10% sodium hydroxide at 10°-14° was slowly added a solution of 4-(p-tolyloxycarbonyl)-butyryl chloride in 50 ml. of ether. The resulting reaction mixture was stirred for an additional three hours. After a work-up similar to that in Example I 7.5 g. (theory, 10.0 g.) of liquid was obtained. The assay according to "active oxygen" content was 81.5% and the corrected yield was 61.2%. After being stored at 0° C for several days the product solidifed and had a melting point of 24°-30° C.

Although the invention has been described in considerable detail with reference to certain preferred embodiments thereof, it will be understood that variations and modifications can be effected within the spirit and scope of the invention as described hereinabove and as defined in the appended claims.

What is claimed is:

1. In the process of preparing a polymer containing an ultraviolet light stabilizer chemically bound to said polymer comprising polymerizing an ethylenically unsaturated monomer capable of being polymerized by free radicals in the presence of a free radical initiator the improvement comprising polymerizing said monomer in the presence of a free radical initiator containing ultraviolet light stabilizing groups and having the formula:

(R-O-O)$_n$R' wherein n is 1 to 4 with provisos (a) through (f) recited below,
a. when n is 1, R and R' are the same or different and are selected from the group consisting of hydrogen, acyl of 2-20 carbons, aroyl of 7-20 carbons, tert-alkyl of 4-12 carbons, tert-cycloalkyl of 4-12 carbons, tertaralkyl of 9-15 carbons, alkoxycarbonyl of 2-20 carbons, cycloalkoxylcarbonyl of 4-20 carbons, carbamoyl, phenylcarbamoyl, alkylcarbamoyl of 2-13 carbons, cycloalkylcarbamoyl of 4-13 carbons, α-hydroxyalkyl of 2-10 carbons, α-hydroxycycloalkyl of 3-10 carbons, α-hydroperoxyalkyl of 2-10 carbons, α-hydroperoxycycloalkyl of 3-10 carbons, alkylsulfonyl of 4-10 carbons, cycloalkylsulfonyl of 3-12 carbons, tert-(alkyloxyalkyl) of 4-20 carbons, tert-(alkoxycycloalkyl) of 4-20 carbons, Q$_3$M, Q$_2$M', diethylphosphate, dimethylphosphate, diphenylphosphinic, di-n-octylphosphate, and dibutyl phosphinic;

wherein

M is selected from silicon, germanium, or tin;
M' is boron; and
Q is alkyl of 1-11 carbons, phenyl, benzyl, or cyclohexyl;

b. when n is 2, R is selected from any of the radicals listed under (a) and R' is selected from the group consisting of carbonyl, alkylidene, of 2-20 carbons, cycloalkylidene of 3-2 carbons, di-tert-alkylene of 6-20 carbons, di-tert-cycloalkylene of 6-20 carbons, di-tert-aralkylene of 12-20 carbons, Q$_2$M<, QM'< wherein

M is selected from silicon, germanium or tin;
M' is boron; and
Q is alkyl of 1-11 carbons, phenyl, benzyl, or cyclohexyl;

c. when n is 3, R is selected from any of the radicals listed under (a) and R' is selected from the group consisting of tert-aralkyl-di-tert-aralkylene of 15-20 carbons, tert-alkylalkylidene of 4-20 carbons, tert-cycloalkylalkylidene of 4-20 carbons, tert-alkylcycloalkylidene of 4-20 carbons, tert-cycloalkylcycloalkylidene of 6-20 carbons, tert-alkyl-di-tert-alkylene of 10-19 carbons, tert-alkyl-di-tert-cycloalkylene of 10-19 carbons, tert-cycloalkyl-di-tert-alkylene of 10-19 carbons, tert-cycloalkyl-di-tert-cycloalkylene of 10-19 carbons, and QM≡wherein M is selected from silicon, germanium or tin; and
Q is selected from alkyl of 1-11 carbons, phenyl, benzyl or cyclohexyl;

d. when n is 4, R is selected from any of the radicals listed under (a) and R' is dialkylidene of 5-16 carbons;

e. only one of R and R' can be hydrogen; and
f. at least one of R and R' contains an ultraviolet light stabilizing radical of a compound selected from the group consisting of

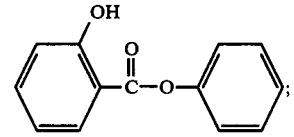

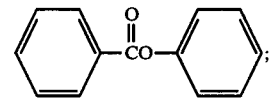

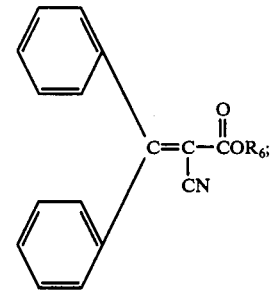

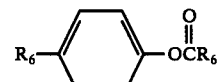

and

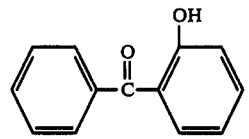

wherein R$_6$ is alkyl of 1-6 carbon atoms.

2. The process of claim 1 wherein the free radical initiator is OO-t-butyl O-2-(2-hydroxybenzoyl) phenyl monoperoxyphthalate.

3. The process of claim 1 wherein the free radical initiator is OO-t-butyl O-p-tolyl monoperoxysuccinate.

4. The process of claim 1 wherein the free radical initiator is di[4-(p-tolyloxycarbonyl)butyryl] peroxide.

5. The process of claim 1 wherein the free radical initiator is 1,3-dimethyl-3-hydroperoxybutyl 2-cyano-3,3-diphenylacrylate.

6. The process of claim 1 wherein the free radical initiator is 1,4-di-[1-(3-(4-benzoyl-3-hydroxyphenoxycarbonyl) propionylperox)-1-methylethyl]benzene.

7. The process of claim 1 wherein the free radical initiator is 1,3,5-tri-[1-(4-(4-benzoyloxyphenoxycarbonyl) butyrylperoxy)-1-methylethyl]benzene.

* * * * *

UNITED STATES PATENT OFFICE
CERTIFICATE OF CORRECTION

Patent No. 4,042,773          Dated August 16, 1977

Inventor(s) Chester S. Sheppard and Ronald E. MacLeay

It is certified that error appears in the above-identified patent and that said Letters Patent are hereby corrected as shown below:

Column 37, line 26, "cycloalkoxylcarbonyl" should read --cycloalkoxycarbonyl--.

Column 37, line 33, "4-10" should read -- 4-20 --.

Column 37, line 34, "(alkyloxyalkyl)" should read -- (alkoxyalkyl) --.

Column 37, line 25, "tertaralkyl" should read -- tert-aralkyl --.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks